US012614620B2

(12) United States Patent
Honda et al.

(10) Patent No.: US 12,614,620 B2
(45) Date of Patent: Apr. 28, 2026

(54) BIOLOGICAL FUNCTION ESTIMATION DEVICE AND BIOLOGICAL FUNCTION ESTIMATION METHOD

(71) Applicant: TERUMO KABUSHIKI KAISHA, Tokyo (JP)

(72) Inventors: Kei Honda, Hadano (JP); Yoshihito Machida, Sagamihara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 178 days.

(21) Appl. No.: 17/951,484

(22) Filed: Sep. 23, 2022

(65) Prior Publication Data

US 2023/0015588 A1 Jan. 19, 2023

Related U.S. Application Data

(63) Continuation of application No. PCT/JP2021/009085, filed on Mar. 8, 2021.

(30) Foreign Application Priority Data

Mar. 27, 2020 (JP) ................................. 2020-059122

(51) Int. Cl.
*G16H 20/10* (2018.01)
*A61B 5/00* (2006.01)
*G16B 5/00* (2019.01)

(52) U.S. Cl.
CPC ........... *G16H 20/10* (2018.01); *A61B 5/4848* (2013.01); *G16B 5/00* (2019.02)

(58) Field of Classification Search
CPC ......... G16H 20/10; A61B 5/4848; G16B 5/00
(Continued)

(56) References Cited

U.S. PATENT DOCUMENTS 5,722,396 A 3/1998 Kotler et al.
5,865,763 A 2/1999 Kotler et al.
(Continued)

FOREIGN PATENT DOCUMENTS

CN 103153184 A 6/2013
CN 105760698 A 7/2016
(Continued)

OTHER PUBLICATIONS

International Search Report (PCT/ISA/210) with translation and Written Opinion (PCT/ISA/237) mailed on May 25, 2021, by the Japan Patent Office as the International Searching Authority for International Application No. PCT/JP2021/009085. (11 pages).
(Continued)

*Primary Examiner* — Jason B Dunham
*Assistant Examiner* — Dawn Trinah Haynes
(74) *Attorney, Agent, or Firm* — Buchanan Ingersoll & Rooney PC

(57) ABSTRACT
A biological function estimation device includes a processor configured to predict a drug reaction in a patient based on an evaluation value obtained by evaluating a biological function of the patient from a test result before drug administration and data on a drug to be administered to the patient, and configured to correct the evaluation value according to a comparison result between an obtained prediction value and a measurement value obtained by measuring the drug reaction after the drug administration.

19 Claims, 10 Drawing Sheets

(58) Field of Classification Search
USPC ............................................................ 705/2
See application file for complete search history.

(56)                    References Cited

U.S. PATENT DOCUMENTS

| | | | | |
|---|---|---|---|---|
| 2009/0137987 | A1* | 5/2009 | Ali ......................... | G16H 20/17 |
| 2011/0046516 | A1 | 2/2011 | Paz et al. | |
| 2012/0041279 | A1 | 2/2012 | Freeman et al. | |
| 2012/0059351 | A1* | 3/2012 | Nordh .................... | G16H 20/10 |
| 2012/0323215 | A1 | 12/2012 | Maier et al. | |
| 2014/0073991 | A1 | 3/2014 | Paz et al. | |
| 2015/0220698 | A1* | 8/2015 | Argyropoulos ........ | G16H 50/30 |
| 2016/0004838 | A1 | 1/2016 | Patterson et al. | |
| 2017/0231561 | A1 | 8/2017 | Sutoko et al. | |
| 2018/0060508 | A1* | 3/2018 | Fokoue-Nkoutche ....................... | |
| | | | | G16H 15/00 |
| 2019/0125902 | A1 | 5/2019 | Rajagopalan et al. | |
| 2019/0171962 | A1* | 6/2019 | Mould ................... | G16H 50/50 |
| 2019/0189260 | A1 | 6/2019 | Ueda et al. | |
| 2021/0318337 | A1* | 10/2021 | Schiffer ................ | G01N 33/68 |

FOREIGN PATENT DOCUMENTS

| | | | |
|---|---|---|---|
| JP | 2000513980 | A | 10/2000 |
| JP | 2008273858 | A | 11/2008 |
| JP | 2010509018 | A | 3/2010 |
| JP | 2013520718 | A | 6/2013 |
| JP | 2018038466 | A | 3/2018 |
| WO | 2019084425 | A1 | 5/2019 |

OTHER PUBLICATIONS

English Translations of the International Search Report (Form PCT/ISA/210) and the Written Opinion of the International Searching Authority (Form PCT/ISA/237) issued May 25, 2021, by the Japan Patent Office in corresponding International Application No. PCT/JP2021/009085. (6 pages).

Office Action/Search Report (The First Office Action) issued on Feb. 26, 2025, in corresponding Chinese Patent Application No. 202180022838.9 and machine English translation of the Office Action. (15 pages).

* cited by examiner

Figure 10:
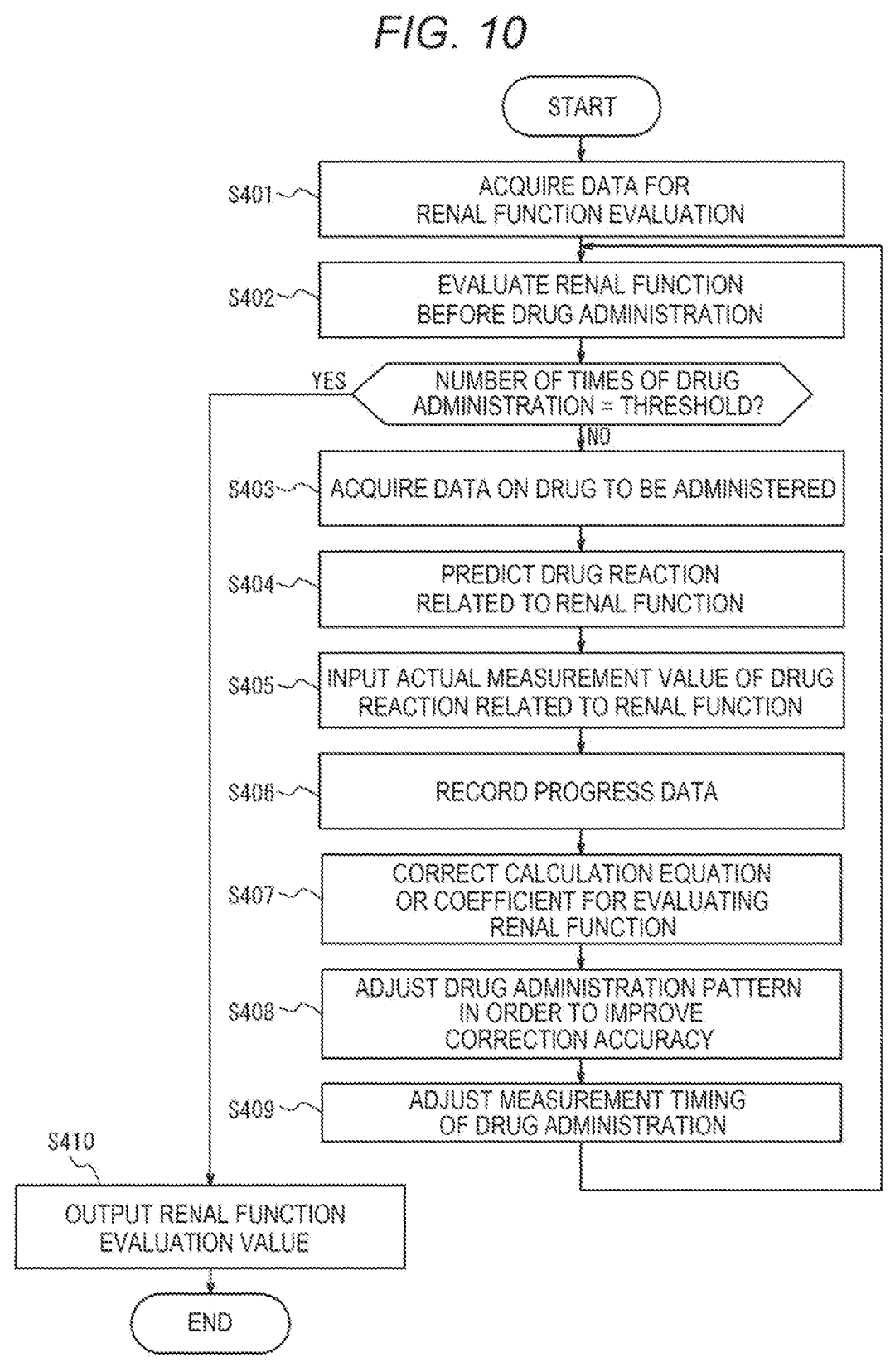

START

S401 — ACQUIRE DATA FOR RENAL FUNCTION EVALUATION

S402 — EVALUATE RENAL FUNCTION BEFORE DRUG ADMINISTRATION

NUMBER OF TIMES OF DRUG ADMINISTRATION = THRESHOLD? — YES / NO

S403 — ACQUIRE DATA ON DRUG TO BE ADMINISTERED

S404 — PREDICT DRUG REACTION RELATED TO RENAL FUNCTION

S405 — INPUT ACTUAL MEASUREMENT VALUE OF DRUG REACTION RELATED TO RENAL FUNCTION

S406 — RECORD PROGRESS DATA

S407 — CORRECT CALCULATION EQUATION OR COEFFICIENT FOR EVALUATING RENAL FUNCTION

S408 — ADJUST DRUG ADMINISTRATION PATTERN IN ORDER TO IMPROVE CORRECTION ACCURACY

S409 — ADJUST MEASUREMENT TIMING OF DRUG ADMINISTRATION

S410 — OUTPUT RENAL FUNCTION EVALUATION VALUE

END

BIOLOGICAL FUNCTION ESTIMATION DEVICE AND BIOLOGICAL FUNCTION ESTIMATION METHOD

CROSS-REFERENCES TO RELATED APPLICATIONS

This application is a continuation of International Application No. PCT/JP2021/009085 filed on Mar. 8, 2021, which claims priority to Japanese Application No. 2020-059122 filed on Mar. 27, 2020, the entire content of both of which is incorporated herein by reference.

TECHNOLOGICAL FIELD

The present disclosure relates to a biological function estimation device and a biological function estimation method.

BACKGROUND DISCUSSION

Japanese Patent Application Publication No. 2013-520718 describes a drug administration system that measures and analyzes values of blood of a patient and calculates drug parameters.

It is important to evaluate a renal function of a hospitalized patient accurately and in real time in order to enhance a therapeutic effect and to help prevent an occurrence of side effects such as renal dysfunction. Unfortunately, in the related art, a satisfactory renal function evaluation is not achieved due to a need for a blood test each time, or due to a problem of characteristics or reliability of an index itself used for evaluation.

SUMMARY

The present disclosure can evaluate a biological function of a patient with relatively high accuracy without requiring a test each time.

A biological function estimation device as an aspect of the present disclosure includes a processor configured to predict a drug reaction in a patient based on an evaluation value obtained by evaluating a biological function of the patient from a test result before drug administration and data on a drug to be administered to the patient, and configured to correct the evaluation value according to a comparison result between an obtained prediction value and a measurement value obtained by measuring the drug reaction after the drug administration.

In an embodiment, the processor is configured to change at least one of an equation and a coefficient for calculating the evaluation value according to the comparison result.

In an embodiment, the data includes at least one of a type, a total administration amount, and an administration amount per unit time of the drug.

In an embodiment, for drug administration at each of a plurality of time points, the processor configured to predict the drug reaction, and to correct the evaluation value according to a comparison result between an obtained new prediction value and a new measurement value obtained by measuring the drug reaction after the drug administration.

In an embodiment, for drug administration at a second time point after a first time point among the plurality of time points, the processor is configured to predict the drug reaction based on a corrected value of the evaluation value obtained for drug administration at the first time point and data on the drug to be administered to the patient at the second time point, and to correct the evaluation value according to a comparison result between an obtained new prediction value and a new measurement value obtained by measuring the drug reaction after the drug administration.

In an embodiment, the processor is configured to record, as temporary correction values, corrected values of the evaluation value obtained for the drug administration at the plurality of time points, and to correct the evaluation value using the recorded temporary correction values.

In an embodiment, the processor is configured to set a drug administration pattern at each of the plurality of time points.

In an embodiment, the processor is configured to adjust, according to a comparison result between a new prediction value and a new measurement value obtained for drug administration at any one of the plurality of time points, the patterns at next and subsequent time points.

In an embodiment, the processor is configured to select, as the pattern, a pattern candidate that is different for each time point from a predetermined pattern candidate group.

In an embodiment, the processor is configured to set the pattern by setting at least one of the number of times of administration of the drug and an administration amount per unit time of the drug.

In an embodiment, the processor is configured to set the pattern by setting a drug administration timing.

In an embodiment, when setting the pattern, the processor is configured to refer to performance data indicating a history of past drug administration and at least one of a prediction value, a measurement value, and a corrected value of an evaluation value.

In an embodiment, the history indicated by the performance data includes a history of another patient.

In an embodiment, the processor is configured to adjust a measurement timing of the drug reaction according to the pattern.

In an embodiment, when predicting the drug reaction, the processor is configured to refer to progress data indicating a history of past drug administration and drug reaction.

In an embodiment, the history indicated by the progress data includes a history of another patient.

In an embodiment, the processor is configured to control a pump configured to administer a drug to the patient.

In an embodiment, the processor is configured to control a sensor configured to measure the drug reaction.

In an embodiment, the biological function estimation device further includes an output unit configured to output the corrected value of the evaluation value.

In an embodiment, the processor is configured to acquire the test result and calculates the evaluation value from the test result.

In an embodiment, the evaluation value is a value obtained by evaluating a renal function as the biological function, and the processor is configured to predict a urine volume as the drug reaction.

A biological function estimation method as an aspect of the present disclosure includes: predicting, by a computer, a drug reaction in a patient based on an evaluation value obtained by evaluating a biological function of the patient from a test result before drug administration and data on a drug to be administered to the patient; administering the drug to the patient by a pump; measuring, by a sensor, the drug reaction after the drug administration; and correcting, by the computer, the evaluation value according to a comparison result between an obtained prediction value and an obtained measurement value.

A biological function estimation method as another aspect of the present disclosure includes: predicting a drug reaction in a patient based on an evaluation value obtained by evaluating a biological function of the patient from a test result before drug administration and data on a drug to be administered to the patient; obtaining a measurement value from an administration of the drug to the patient; and correcting the evaluation value according to a comparison result between an obtained prediction value and the obtained measurement value.

According to the present disclosure, a biological function of a patient can be evaluated with relatively high accuracy without requiring a test each time.

BRIEF DESCRIPTION OF THE DRAWINGS

FIG. 2 is a block diagram showing a configuration of a biological function estimation device according to an aspect of the present disclosure.

FIG. 10 is a flowchart showing an operation of a biological function estimation device according to the fourth embodiment.

DETAILED DESCRIPTION

Figure 1:
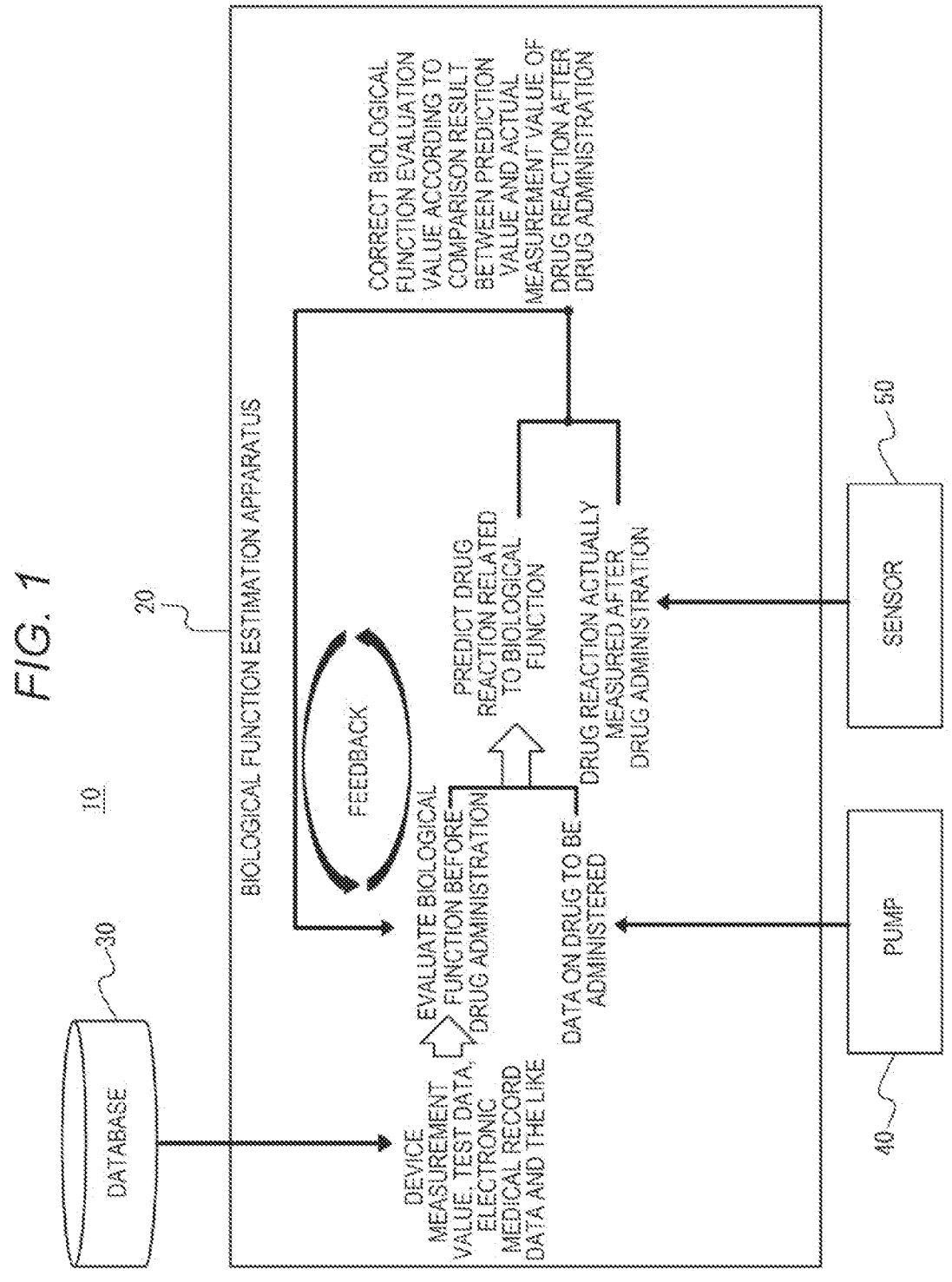
FIG. 1 is a diagram showing a configuration and functions of a system as an aspect of the present disclosure.

Set forth below with reference to the accompanying drawings is a detailed description of embodiments of a biological function estimation device and a biological function estimation method. Note that since embodiments described below are preferred specific examples of the present disclosure, although various technically preferable limitations are given, the scope of the present disclosure is not limited to the embodiments unless otherwise specified in the following descriptions.

In the drawings, the same or corresponding parts are denoted by the same reference numerals. In the description of the embodiments, the description of the same or corresponding parts will be omitted or simplified as appropriate.

A configuration of a system 10 as an aspect of the present disclosure will be described with reference to FIG. 1.

The system 10 shown in FIG. 1 includes a biological function estimation device 20, a database 30, a pump 40, and a sensor 50.

The biological function estimation device 20 is communicably connected to the database 30, the pump 40, and the sensor 50 directly or via a network such as a local area network (LAN).

The biological function estimation device 20 can be installed in a hospital as an example, and may be installed in another facility such as a data center. The biological function estimation device 20 can be, for example, a general-purpose computer such as a personal computer (PC) or a server computer, or a dedicated computer.

The database 30 can be installed in a hospital as an example, and may be installed in another facility such as a data center. The database 30 can be, for example, a relational database management system (RDBMS). The database 30 can be separate from the biological function estimation device 20 as an example, or may be integrated with the biological function estimation device 20.

The pump 40 can be installed in a hospital. The pump 40 can be, for example, an infusion pump or a syringe pump. The pump 40 may be a smart pump.

The sensor 50 can be installed in a hospital. The sensor 50 can be, for example, a urine volume sensor, a body temperature sensor, a blood pressure sensor, a pulse sensor, or a respiration sensor.

Figure 2:
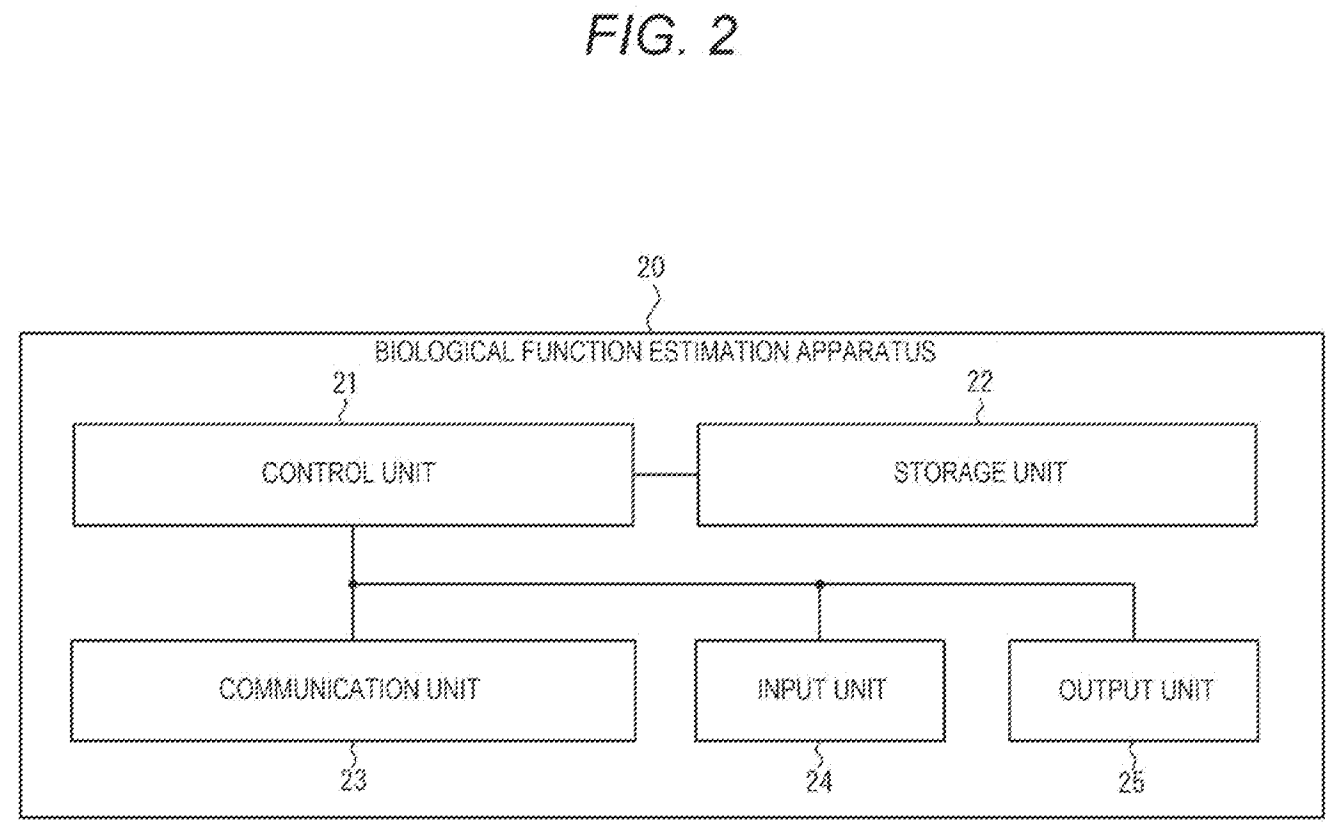

A configuration of the biological function estimation device 20 as an aspect of the present disclosure will be described with reference to FIG. 2.

The biological function estimation device 20 includes a control unit 21, a storage unit 22, a communication unit 23, an input unit 24, and an output unit 25.

The control unit 21 includes at least one processor, at least one dedicated circuit, or a combination of at least one processor and at least one dedicated circuit. The processor can be a general-purpose processor such as a central processing unit (CPU) or a graphics processing unit (GPU), or a dedicated processor specialized for specific processing. The dedicated circuit can be, for example, a field-programmable gate array (FPGA) or an application specific integrated circuit (ASIC). The control unit 21 executes processing related to an operation of the biological function estimation device 20 while controlling the units of the biological function estimation device 20.

The storage unit 22 includes at least one semiconductor memory, at least one magnetic memory, at least one optical memory, or a combination of at least two types of the memories. The semiconductor memory can be, for example, a random access memory (RAM) or a read only memory (ROM). The RAM can be, for example, a static random access memory (SRAM) or a dynamic random access memory (DRAM). The ROM can be, for example, an electrically erasable programmable read only memory (EEPROM). The storage unit 22 functions as, for example, a main storage device, an auxiliary storage device, or a cache memory. The storage unit 22 stores data used for the operation of the biological function estimation device 20 and data obtained by the operation of the biological function estimation device 20. The database 30 may be integrated with the biological function estimation device 20 by being constructed in the storage unit 22.

The communication unit 23 includes at least one communication interface. The communication interface can be, for example, a LAN interface. The communication unit 23 receives the data used for the operation of the biological function estimation device 20 and transmits the data obtained by the operation of the biological function estimation device 20.

The input unit 24 includes at least one input interface. The input interface can be, for example, a physical key, a capacitive key, a pointing device, a touch screen provided integrally with a display, or a microphone. The input unit 24 receives an operation of inputting the data used for the operation of the biological function estimation device 20. The input unit 24 may be connected to the biological function estimation device 20 as an external input device instead of being provided in the biological function estimation device 20. For example, any method such as universal serial bus (USB), high-definition multimedia interface (HDMI®), or Bluetooth® can be used as a connection method.

The output unit 25 includes at least one output interface. The output interface can be, for example, a display or a speaker. The display can be, for example, a liquid crystal display (LCD) or an organic electro luminescence (EL) display. The output unit 25 outputs the data obtained by the operation of the biological function estimation device 20. The output unit 25 may be connected to the biological function estimation device 20 as an external output device instead of being provided in the biological function estimation device 20. For example, any method such as USB, HDMI, or Bluetooth can be used as a connection method.

A function of the biological function estimation device 20 is implemented by executing a program as an aspect of the present disclosure by a processor corresponding to the control unit 21. That is, the function of the biological function estimation device 20 is implemented by software. The program causes a computer to function as the biological function estimation device 20 by causing the computer to execute the operation of the biological function estimation device 20. That is, the computer functions as the biological function estimation device 20 by executing the operation of the biological function estimation device 20 according to the program.

The program can be stored in a non-transitory computer-readable medium. The non-transitory computer-readable medium can be, for example, a magnetic recording device, an optical disc, a magneto-optical recording medium, or a ROM. Distribution of the program is executed by, for example, selling, transferring, or lending a portable medium such as a digital versatile disc (DVD) or a compact disc read only memory (CD-ROM) in which the program is stored. The program may be distributed by storing the program in a storage of a server and transferring the program from the server to another computer. The program may be provided as a program product.

For example, the computer temporarily stores, in a main storage device, the program stored in the portable medium or the program transferred from the server. Then, the computer reads, by the processor, the program stored in the main storage device, and executes, by the processor, processing according to the read program. The computer may read the program directly from the portable medium and execute processing according to the program. Each time the program is transferred from the server to the computer, the computer may sequentially execute processing according to the received program. The processing may be executed by a so-called application service provider (ASP) type service in which the function is implemented only by instruction execution and result acquisition without transferring the program from the server to the computer. The program includes information that is provided for processing by an electronic computer and that is treated equivalent to a program. For example, data that is not a direct command to the computer but has a property that defines processing of the computer corresponds to "data that is treated equivalent to a program".

A part or all of the functions of the biological function estimation device 20 may be implemented by a dedicated circuit corresponding to the control unit 21. That is, a part or all of the functions of the biological function estimation device 20 may be implemented by hardware.

Functions of the system 10 as an aspect of the present disclosure will be described with reference to FIGS. 1 and 2. The functions correspond to a biological function estimation method as an aspect of the present disclosure.

The database 30 stores in-hospital data such as device measurement values, test data, and electronic medical record data. The test data can include a test result before drug administration.

The control unit 21 of the biological function estimation device 20 acquires, via the communication unit 23, the in-hospital data from the database 30. The control unit 21 evaluates a biological function of a patient based on the test result before the drug administration, which is provided in the in-hospital data. As a result of the evaluation of the biological function of the patient based on the test result before the drug administration, an evaluation value Ve can be obtained. The biological function can be, for example, an internal function such as a renal function, a cardiac function, a lung function, or a liver function. For the evaluation on the biological function, not only the test result before the drug administration, but also the device measurement values and the electronic medical record data before the drug administration, which are provided in the in-hospital data, may be used. As a modification, the biological function of the patient may be evaluated by a device different from the biological function estimation device 20. That is, the control unit 21 of the biological function estimation device 20 may acquire, via the communication unit 23, the evaluation value Ve from another device that evaluates the biological function of the patient based on the test result before the drug administration.

The control unit 21 of the biological function estimation device 20 acquires, via the communication unit 23, data Dm on a drug to be administered to the patient from the pump 40 or a device that monitors and controls the pump 40. The data Dm includes at least one of a type, a total administration amount, and an administration amount per unit time of the drug.

The control unit 21 of the biological function estimation device 20 predicts a drug reaction in the patient based on the evaluation value Ve and the data Dm on the drug. As a result, a prediction value Vp is obtained. The drug reaction can be, for example, a vital sign such as a urine volume, a body temperature, a blood pressure, a pulse, or respiration, or a change in the vital sign.

The pump 40 administers the drug to the patient. The sensor 50 can measure the drug reaction after the drug administration. As a result, a measurement value Vm (i.e., an actual measurement value Vm) can be obtained.

The control unit 21 of the biological function estimation device 20 acquires, via the communication unit 23, the measurement value Vm from the sensor 50.

The control unit 21 of the biological function estimation device 20 corrects the evaluation value Ve according to a comparison result between the prediction value Vp and the measurement value Vm.

According to the above aspect, the biological function of the patient can be evaluated with relatively high accuracy without requiring a test each time.

Hereinafter, some embodiments as specific examples of the aspect shown in FIGS. 1 and 2 will be described with reference to the drawings.

First Embodiment

Figure 3:
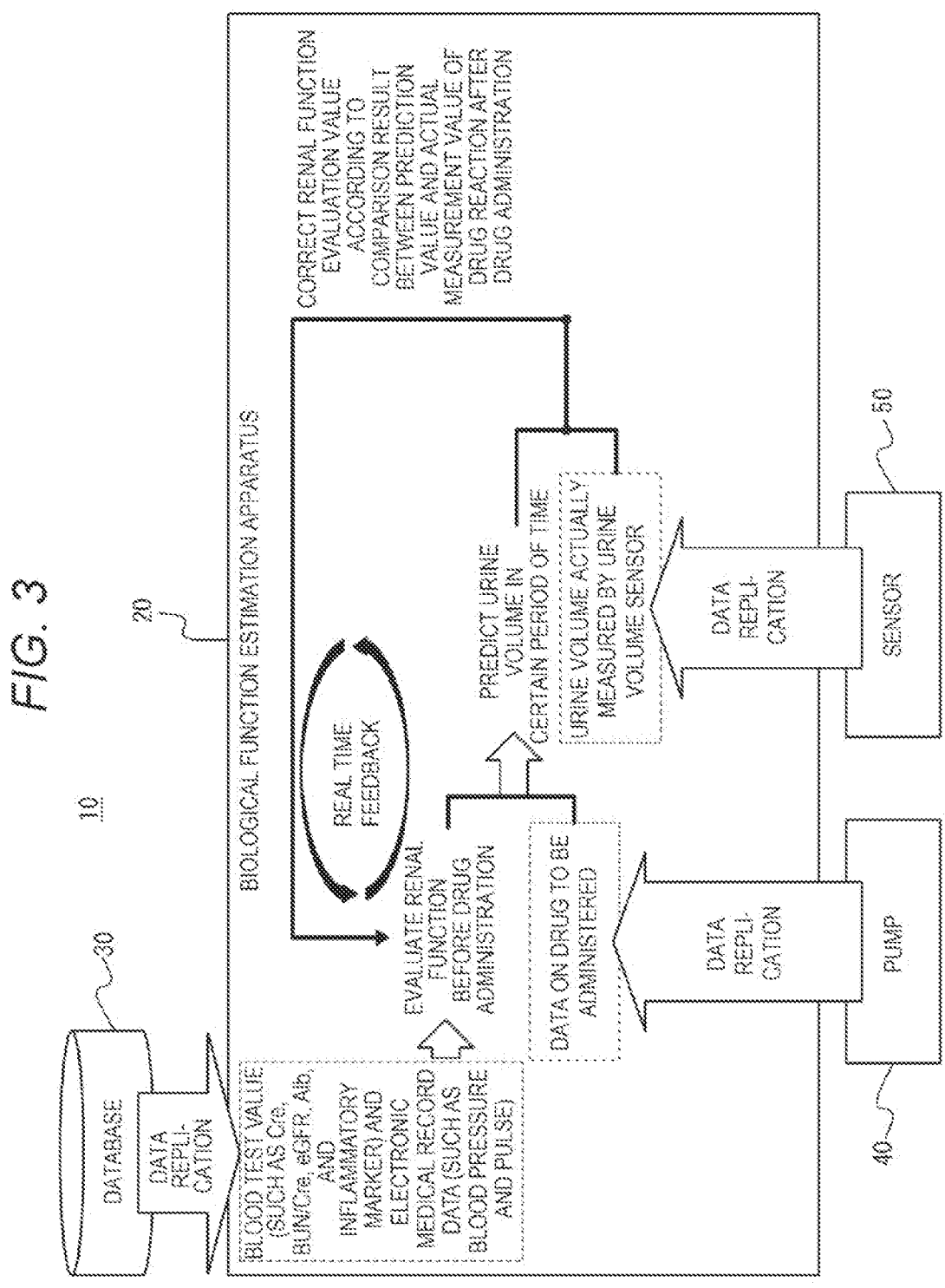
FIG. 3 is a diagram showing a configuration and functions of a system according to a first embodiment.

In the present embodiment, as shown in FIG. 3, the in-hospital data stored in the database 30 can include a blood test value as a test result before the drug administration. The blood test value provided in the in-hospital data can include, for example, Cre, BUN/Cre, eGFR, Alb, or an inflammatory marker. "Cre" is a value of creatinine. "BUN/Cre" is a value obtained by dividing a concentration of urea nitrogen contained in blood by a concentration of creatinine. "eGFR" is an estimated glomerular filtration rate. "Alb" is a value of albumin. The blood test value provided in the in-hospital data may be Cys-C. "Cys-C" is a value of serum cystatin C. Electronic medical record data provided in the in-hospital data can be, for example, blood pressure or pulse.

In the present embodiment, the evaluation value Ve is a value obtained by evaluating a renal function as a biological function. The evaluation value Ve can be, for example, a glomerular filtration rate (GFR) or an eGFR. The control unit 21 of the biological function estimation device 20 predicts a urine volume per unit time as a drug reaction. The sensor 50 can measure a urine volume per unit time as a drug reaction. That is, the sensor 50 can be a urine volume sensor.

Figure 4:
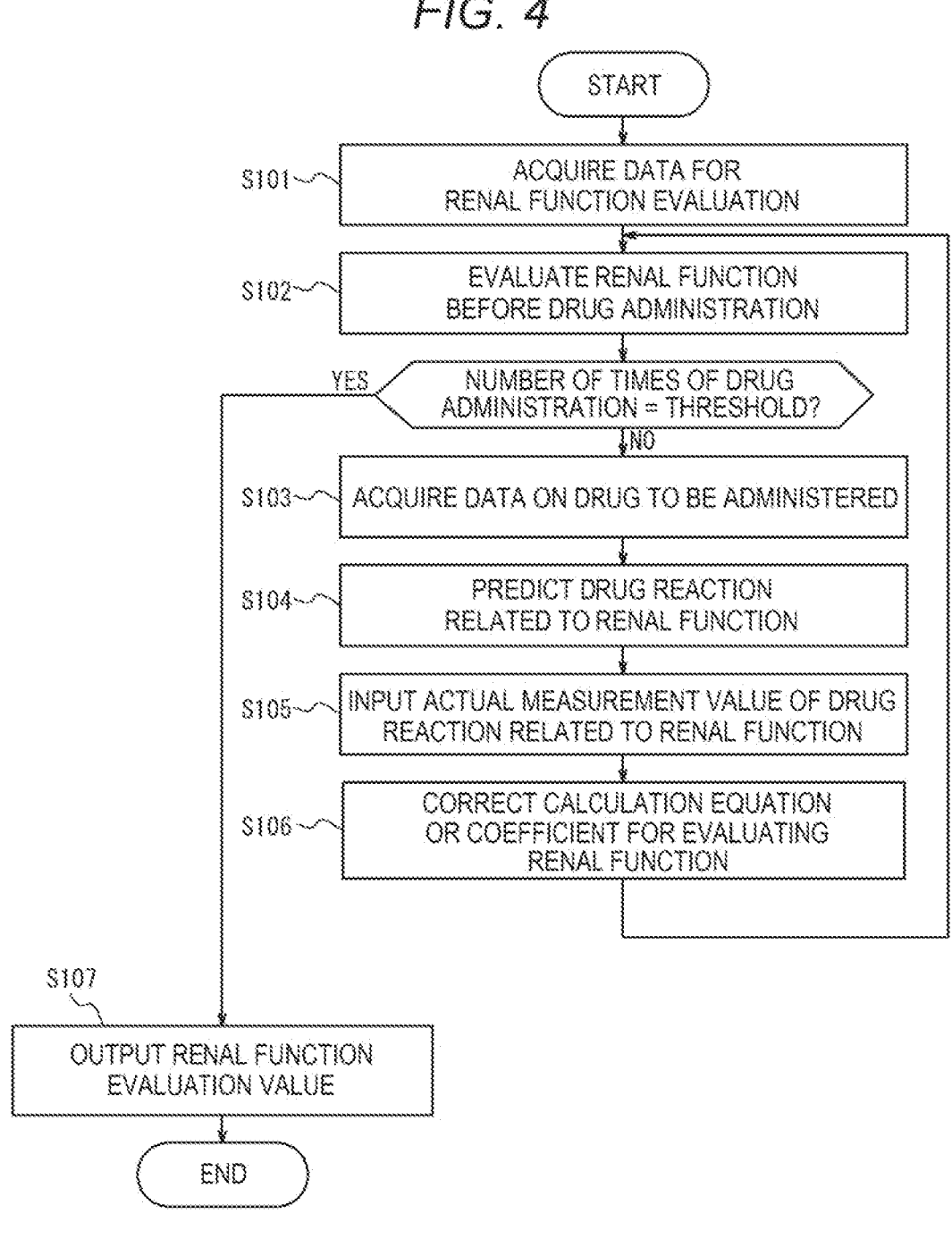
FIG. 4 is a flowchart showing an operation of a biological function estimation device according to the first embodiment.

An operation of the biological function estimation device 20 according to the present embodiment will be described with reference to FIG. 4.

In S101, the control unit 21 acquires a test result before the drug administration. Specifically, the control unit 21 acquires, via the communication unit 23, data for renal function evaluation such as the blood test value and the electronic medical record data that are provided in the in-hospital data from the database 30. As a modification, the control unit 21 may receive, via the input unit 24 such as a touch screen, an input of the data for renal function evaluation from a user such as a doctor or a nurse. Alternatively, the control unit 21 may receive, via the electronic medical record data or the input unit 24 such as a touch screen, an input of presence or absence of a disease to be considered at the time of renal function evaluation, such as presence of thyroid dysfunction or some malignant tumor diseases.

In S102, the control unit 21 evaluates a renal function of a patient before the drug administration based on the test result acquired in S101. That is, the control unit 21 calculates the evaluation value Ve based on the test result before the drug administration. For example, the control unit 21 calculates the GFR or the eGFR by substituting, into an equation for renal function evaluation, the blood test value and a value of the electronic medical record data that are provided in the data acquired in S101. Alternatively, the control unit 21 calculates the GFR by multiplying, by a coefficient, the eGFR provided in the data acquired in S101. In a case of the former calculation, for unquantified information such as presence or absence of a disease, information in a state normalized or quantified in a form that can be substituted into an equation is substituted into the equation. The control unit 21 stores the obtained evaluation value Ve in the storage unit 22.

After S102, if the number of times of administration of the drug (i.e., drug administration) does not reach a threshold Vt, the processing of S103 is executed. The threshold Vt may be any value of 1 or more, and can be, for example, set to a value of 2 or more in the present embodiment.

In S103, the control unit 21 acquires the data Dm on a drug to be administered to the patient. Specifically, the control unit 21 acquires, via the communication unit 23, the data Dm on the drug to be administered from the pump 40 or a device that monitors and controls the pump 40. As a modification, the control unit 21 may receive, via the input unit 24 such as a touch screen, an input of the data Dm on the drug from a user such as a doctor or a nurse.

In S104, the control unit 21 can predict, based on the evaluation value Ve obtained in S102 and the drug data Dm acquired in S103, a urine volume per unit time as a drug reaction related to the renal function of the patient. Specifically, the control unit 21 refers to a table stored in advance in the storage unit 22, and specifies the prediction value Vp corresponding to a combination of the evaluation value Ve and at least one of a type, a total administration amount, and an administration amount per unit time of the drug that are provided in the data Dm on the drug. Alternatively, the control unit 21 calculates the prediction value Vp by substituting, into a predefined equation, the evaluation value Ve and at least one of the type, the total administration amount, and the administration amount per unit time of the drug that are provided in the data Dm on the drug.

In S105, after the drug administration by the pump 40 for a certain period of time, the control unit 21 acquires, by the sensor 50, a result of measuring the urine volume per unit time as the drug reaction related to the renal function of the patient. Specifically, the control unit 21 acquires, via the communication unit 23, the measurement value Vm from the sensor 50. As a modification, the control unit 21 may receive, via the input unit 24 such as a touch screen, an input of the measurement value Vm from a user such as a doctor or a nurse.

In S106, the control unit 21 corrects the evaluation value Ve obtained in S102 according to a comparison result between the prediction value Vp obtained in S104 and the measurement value Vm obtained in S105. Specifically, the control unit 21 changes at least one of the equation and the coefficient for calculating the evaluation value Ve in S102 according to the comparison result between the prediction value Vp and the measurement value Vm. For example, the control unit 21 corrects the equation for renal function evaluation applied in S102 such that a difference between the prediction value Vp and the measurement value Vm becomes relatively small. Alternatively, when there are a plurality of equations for renal function evaluation that can be applied in S102, the control unit 21 reselects an equation to be used such that the difference between the prediction value Vp and the measurement value Vm becomes relatively small. Alternatively, the control unit 21 corrects the coefficient to be multiplied to the eGFR in S102 such that the difference between the prediction value Vp and the measurement value Vm becomes relatively small. Then, in S102, the control unit 21 recalculates the evaluation value Ve using at least one of the corrected equation and coefficient. For example, the control unit 21 recalculates the GFR or the eGFR by substituting, into the corrected equation for renal function evaluation, the blood test value and the value of the electronic medical record data that are provided in the data acquired in S101. That is, the control unit 21 corrects the GFR or the eGFR. Alternatively, the control unit 21 recalculates the GFR by multiplying, by the corrected coefficient, the eGFR provided in the data acquired in S101. That is, the control unit 21 corrects the GFR. The control unit 21 overwrites the evaluation value Ve stored in the storage unit 22 with the corrected value.

After S102, if the number of times of administration of the drug reaches the threshold Vt, the processing of S107 is executed.

In S107, the output unit 25 outputs the corrected value of the evaluation value Ve. Specifically, the control unit 21 displays, on the output unit 25 such as a display, the corrected value of the evaluation value Ve that is overwritten and stored in the storage unit 22.

In the present embodiment, since the threshold Vt can be set, for example, to a value of 2 or more, the drug is administered to the patient at a plurality of time points. For drug administration at each of the plurality of time points, the control unit 21 can predict a drug reaction, and can correct the evaluation value Ve according to a comparison result between the obtained new prediction value Vp and the new measurement value Vm obtained by measuring the drug reaction after the drug administration. Specifically, for drug administration at a second time point after a first time point among the plurality of time points, the control unit 21 can predict a drug reaction based on a corrected value of the evaluation value Ve obtained for the drug administration at the first time point and the data Dm on the drug to be administered to the patient at the second time point, and further can correct the evaluation value Ve according to a comparison result between the obtained new prediction value Vp and the new measurement value Vm obtained by measuring the drug reaction after the drug administration.

For example, for drug administration at a time point T1, the control unit 21 executes the processing of S103 to S106 to correct the evaluation value Ve. As a result, in S102, a corrected value of the evaluation value Ve can be obtained. For drug administration at a next time point T2, the control unit 21 executes the processing of S103 to S106 to correct the corrected value of the evaluation value Ve. That is, the control unit 21 further corrects the evaluation value Ve. As a result, in S102, a further corrected value of the evaluation value Ve is obtained. When the threshold Vt=n and n>2, for drug administration from a next time point T3 to a time point Tn, the control unit 21 also executes the processing of S103 to S106 to further correct the evaluation value Ve. In this way, in the present embodiment, the control unit 21 recursively corrects the evaluation value Ve.

As a modification of the present embodiment, the control unit 21 may record, as temporary correction values, corrected values of the evaluation value Ve obtained for drug administration at a plurality of time points, and may further correct the evaluation value Ve using the recorded temporary correction values.

For example, for the drug administration at one or more time points, the control unit 21 executes the processing of S103 to S106 to recursively correct the evaluation value Ve. In S107, the control unit 21 records a recursively corrected value of the evaluation value Ve as a temporary correction value C1. For the drug administration at another time point among the one or more time points, the control unit 21 also executes the processing of S103 to S106 to recursively correct the evaluation value Ve. In S107, the control unit 21 records a recursively corrected value of the evaluation value Ve as a temporary correction value C2. As a result, a plurality of temporary correction values are recorded. The number of temporary correction values, for example, may be three or more. The control unit 21 determines a final output value of the evaluation value Ve using the plurality of temporary correction values. That is, the control unit 21 further corrects the evaluation value Ve. Any method such as average value calculation, median value calculation, single regression analysis, multiple regression analysis, polynomial regression, or regularization can be used as a method for determining the final output value.

As described above, in the present embodiment, the control unit 21 of the biological function estimation device 20 predicts the urine volume of the patient based on the evaluation value Ve obtained by evaluating the renal function of the patient from the test result before drug administration and the data Dm on the drug to be administered to the patient. The control unit 21 corrects the evaluation value Ve according to the comparison result between the obtained prediction value Vp and the measurement value Vm obtained by measuring the urine volume after drug administration.

According to the present embodiment, the renal function of a patient can be evaluated with relatively high accuracy without requiring a test each time.

In the present embodiment, whether to execute the processing of S103 or the processing of S107 can be selected depending on whether the number of times of administration of the drug reaches the threshold Vt. Alternatively, the difference between the prediction value Vp and the measurement value Vm may be used instead of the number of times of administration of the drug. That is, when the difference between the prediction value Vp and the measurement value Vm is greater than a specific threshold, the processing of S103 may be selected, and, for example, when the difference between the prediction value Vp and the measurement value Vm is equal to or less than the specific threshold, the processing of S107 may be selected.

Alternatively, both the threshold Vt for the number of times of administration of the drug and the threshold for the difference between the prediction value Vp and the measurement value Vm may be used. In this case, a condition for selecting the processing of S107 may be set as a case where both of the thresholds are satisfied. Alternatively, the processing of S107 may be selected if the threshold Vt for the number of times of administration of the drug is satisfied when the difference between the prediction value Vp and the measurement value Vm is not less than the specific threshold (i.e., greater than or equal to the specific threshold). Alternatively, the processing of S107 may be selected if the difference between the prediction value Vp and the measurement value Vm is less than the specific threshold when the threshold Vt for the number of times of administration of the drug is not satisfied. By combining the two thresholds in this way, it is possible to obtain a renal function evaluation value with relatively high accuracy while setting an upper limit value of a time required to output the renal function evaluation value according to a use scene.

The most accurate index of renal function evaluation, for example, can be a GFR obtained by measuring an excretion rate of inulin from glomeruli. However, inulin is not present in the body. Therefore, inulin needs to be administered by infusion for measurement, and precise urine collection or complete urination and frequent blood collection are required. In this way, the measurement on GFR may be complicated and may also be accompanied by a burden on the patient. Therefore, the GFR is not used in clinical practice except when precise renal function evaluation is required for patients with renal disease or renal transplant donors.

At present, an alternative marker can be used.

An estimated creatinine clearance (eCCr) calculated by substituting, into an estimation equation, a serum concentration of creatinine, which is an effluent from a living body, a body weight, age, and sex is used. Alternatively, the eGFR calculated from serum Cre, age, and sex is used. Measured CCr can be set as the measurement value, and the measurement on creatinine clearance (CCr) requires blood collection and accurate measurement on the urine volume for 24 hours. Therefore, it is extremely rare that the CCr is generally measured in order to obtain a drug administration guideline in clinical practice.

As a result, what is executed as renal function evaluation in clinical practice can be a measurement on serum Cre and calculation on eCCr or eGFR. However, since these operations require a blood test, a limit in execution frequency may exist, and the renal function may not be able to be evaluated in real time. Further, the calculated eCCr or eGFR may not be accurate. Unlike inulin, creatinine is secreted not only by glomerular filtration but also by renal tubule. Therefore, the CCr can be higher than the GFR, for example, by about 20% to 30%. In addition, with respect to the serum Cre, no decrease in renal function may be detected in a sarcopenia patient having a decreased muscle mass and in many older people. That is, it is expressed that the renal function is good. At or above 85 years old, for example, 50% or more is said to be sarcopenia. The prevalence of sarcopenia, for example, in Japan is about 3,700,000. In addition, in the intensive care unit (ICU), even when the patient is relatively young, since he or she may be bedridden for a while, the muscle mass of the patient can decrease. When the eCCr or eGFR is calculated using the serum Cre for such a patient, a renal function evaluation value may be calculated to be relatively higher than a true value.

If administration is executed without accurately evaluating the renal function, there is a risk that a side effect may occur by administering a normal amount of a renal excretion drug to a patient with a decreased renal function, or a risk that a drug-induced renal disorder may occur. In particular, for example, when the calculated eCCr or eGFR is between, for example, about 60 mL/min to 100 mL/min, it can be difficult to determine whether a patient has a normal renal function or a patient has a normal laboratory values with actually poor renal function. In addition, if a physician mistakenly administers the same dose of medication to a patient with abnormal renal function as to a normal patient, this can lead to renal dysfunction. For example, particularly appropriate renal function evaluation is required for a patient of chronic kidney disease (CKD).

In addition, the Cys-C or BUN/Cre is available as renal function evaluation executed in a clinical practice, but since a blood test is required each time similar as the Cre, the eCCr, and the eGFR, the Cys-C or BUN/Cre is not suitable for real-time renal function evaluation. In addition, there also can be a problem in measurement accuracy for Cys-C and BUN/Cre.

The serum cystatin C is expressed in the entirety of the body of a patient, a production amount and rate of production of serum cystatin C are generally constant. In addition, serum cystatin C is generally not influenced by external factors such as inflammation and age. Further, after cystatin C secreted to the outside of cells is subjected to glomerular filtration in a relatively short time, 99% of the cystatin C is reabsorbed and catabolized by proximal tubules. Therefore, the cystatin C is not recirculated into the blood. Therefore, it is considered that the serum Cys-C is determined by the glomerular filtration rate. However, it is known that the prediction accuracy on eGFR decreases in a patient with end-stage renal disease. In addition, it is suggested that the serum Cys-C can be higher than a true value in a patient administered with steroid in a relatively high capacity or over a long term. Furthermore, the serum Cys-C is considered to be affected by the presence of thyroid dysfunction or some malignant tumor diseases.

Since the serum CCr is used for the BUN/Cre, the BUN/Cre has the same problem as the serum CCr.

According to the present embodiment, by adopting one or more feedback systems, the renal function can be more accurately estimated without using a blood test. Further, since feedback is executed in real time, the renal function of a patient during hospitalization can be evaluated relatively accurately and in real time.

Second Embodiment

Differences from the first embodiment will be mainly described.

Figure 5:
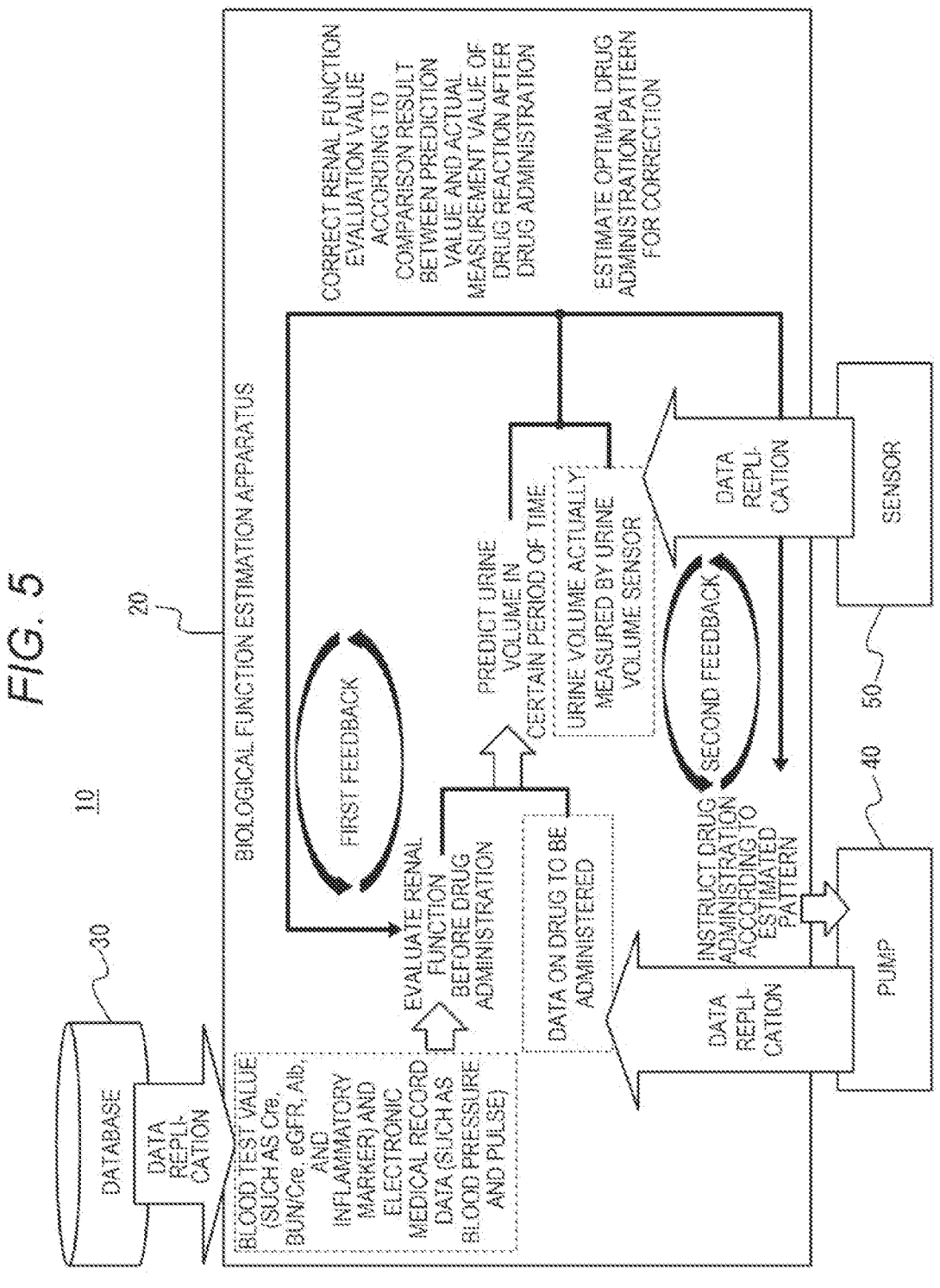
FIG. 5 is a diagram showing a configuration and functions of a system according to a second embodiment.

In the present embodiment, as shown in FIG. 5, in order to improve the evaluation accuracy on the renal function, an optimal drug administration pattern for correcting the evaluation value Ve is estimated, and drug administration is instructed according to the estimated pattern. At least one of a pattern in which a dose of a drug is increased stepwise from a low dose and a pattern in which the dose of the drug is decreased stepwise from a high dose within a predetermined prescription range is selected as the drug administration pattern. Therefore, a total amount of the drug to be administered can be as prescribed.

Figure 6:
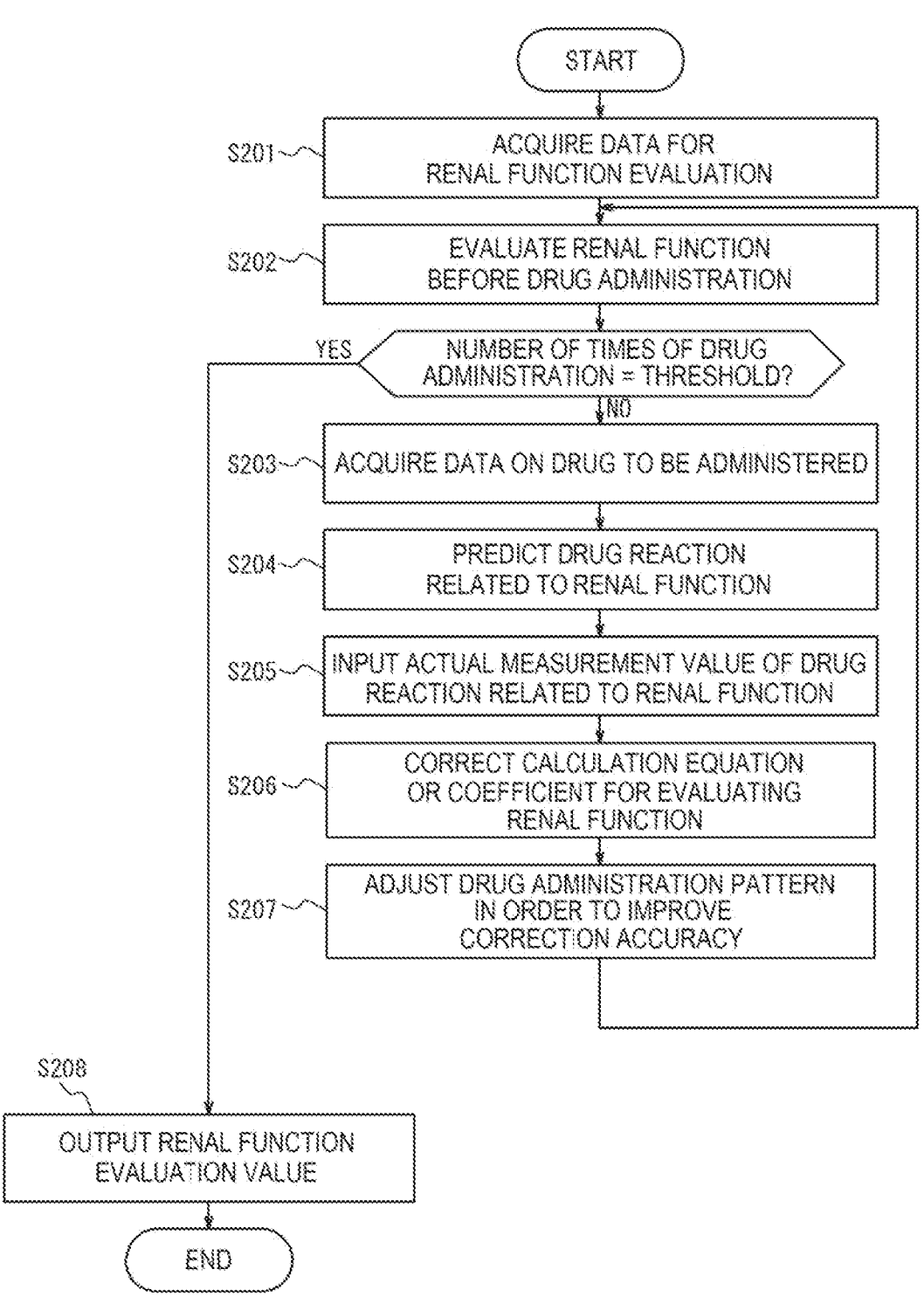
FIG. 6 is a flowchart showing an operation of a biological function estimation device according to the second embodiment.

An operation of the biological function estimation device 20 according to the present embodiment will be described with reference to FIG. 6.

Since processing of S201 to S206 is the same as the processing of S101 to S106 in the first embodiment, the description of S201 to S206 will be omitted.

In S207, the control unit 21 adjusts next and subsequent drug administration patterns according to a comparison result between the prediction value Vp obtained in step S204 and the measurement value Vm obtained in S205. Specifically, the control unit 21 controls the pump 40 to set at least one of the number of times of administration of the drug and the administration amount per unit time of the drug, thereby setting the drug administration pattern to the above pattern.

In the present embodiment, the control unit 21 refers to a plurality of drug administration patterns stored in advance in the storage unit 22 and adjusts the drug administration pattern in S207. When a difference between the prediction value Vp and the measurement value Vm does not converge even when the processing of S202 to S206 are repeated because the prediction value Vp obtained in S202 continues to vary, an optimal drug administration pattern for obtaining a stable prediction value Vp can be selected.

When the prediction value Vp obtained in S202 greatly varies each time the processing of S202 to S206 is executed, a main reason may be that a magnitude of the measurement value Vm obtained in S205 is not appropriate. When the urine volume per unit time as the measurement value Vm is too small, a measurement value tends to vary due to an error in measurement, and variation occurs in the prediction value Vp calculated based on the measurement value. On the other hand, when the urine volume per unit time is too large, since a variation amount in the urine volume that occurs while the processing of S201 to S206 are repeated also increases, the prediction value Vp can greatly vary. The urine volume per unit time is determined by a balance between the renal function and the drug administration amount. Therefore, by executing administration in which the dose of the drug is increased stepwise from a relatively low dose or administration in which the dose of the drug is decreased stepwise from a relatively high dose within a predetermined prescription range, it is possible to obtain a measurement point at which the urine volume is not too small and is not too large. As a result, it is possible to obtain a stable prediction value Vp.

A plurality of drug administration patterns are stored in the storage unit 22, and the dose of the drug can be increased stepwise from a relatively low dose, and the dose of the drug can be decreased stepwise from a relatively high dose. In addition, for example, when the dose of the drug is increased stepwise from a relatively low dose, it is possible to select various drug administration patterns having different lengths of time for maintaining the relatively low dose and the relatively high dose. By using the optimal drug administration pattern, it is possible to acquire a larger number of measurement points at which the optimal measurement value Vm for obtaining the prediction value Vp can be obtained within a range in which a necessary drug efficacy is not reduced.

An optimal drug administration pattern can be automatically selected as the drug administration pattern in S207 according to a value of a difference between the prediction value Vp obtained in S204 and the measurement value Vm obtained in S205, a magnitude of the measurement value Vm, and a variation amount in the measurement value Vm. In addition, it is possible to designate, via the input unit 24 such as a touch screen, a drug administration pattern to be used or a drug administration pattern not to be used based on a patient state or past performance, and it is also possible to set in advance a drug administration pattern to be preferentially used.

In the present embodiment, the control unit 21 stores the measurement value Vm in the storage unit 22 and calculates the variation amount in the measurement value Vm. A generally used calculation method such as a method for calculating a difference from a previous value, a method of using time differentiation of the measurement value Vm, or a method of evaluating standard deviation or variation can be used as a method for calculating the variation amount.

Since the processing of S208 is the same as the processing of step S107 in the first embodiment, the description of S208 will be omitted.

As described above, in the present embodiment, the control unit 21 sets a drug administration pattern at each of a plurality of time points. Specifically, the control unit 21 adjusts the drug administration patterns at next and subsequent time points according to a comparison result between the new prediction value Vp and the new measurement value Vm obtained for drug administration at any one of the plurality of time points.

According to the present embodiment, even when the measurement value Vm is temporarily not within an appropriate range for obtaining the prediction value Vp and the prediction value Vp continues to vary, the optimum drug administration pattern for obtaining the stable prediction value Vp can be selected. Therefore, the estimation accuracy and the measurement efficiency on the renal function can be improved.

In the present embodiment, whether to execute the processing of S203 or the processing of S208 can be selected depending on whether the number of times of administration of the drug reaches the threshold Vt. Alternatively, the difference between the prediction value Vp and the measurement value Vm may be used instead of the number of times of administration of the drug, as in the first embodiment. Alternatively, both the threshold Vt for the number of times of administration of the drug and the threshold for the difference between the prediction value Vp and the measurement value Vm may be used. In any case, an appropriate drug administration pattern is selected by the processing of S207 based on the difference between the prediction value Vp and the measurement value Vm, the magnitude of the measurement value Vm itself, or the variation amount in the measurement value Vm.

As a modification of the present embodiment, the control unit 21 may select, as the drug administration pattern, a pattern candidate that is different for each time point from a predetermined pattern candidate group.

As a modification of the present embodiment, when setting the drug administration pattern, the control unit 21 may refer to the performance data Da indicating a history of past drug administration and at least one of the prediction value Vp, the measurement value Vm, and the corrected value of the evaluation value Ve. The history indicated by the performance data Da may include a history of another patient.

Third Embodiment

Differences from the first embodiment will be mainly described.

Figure 7:
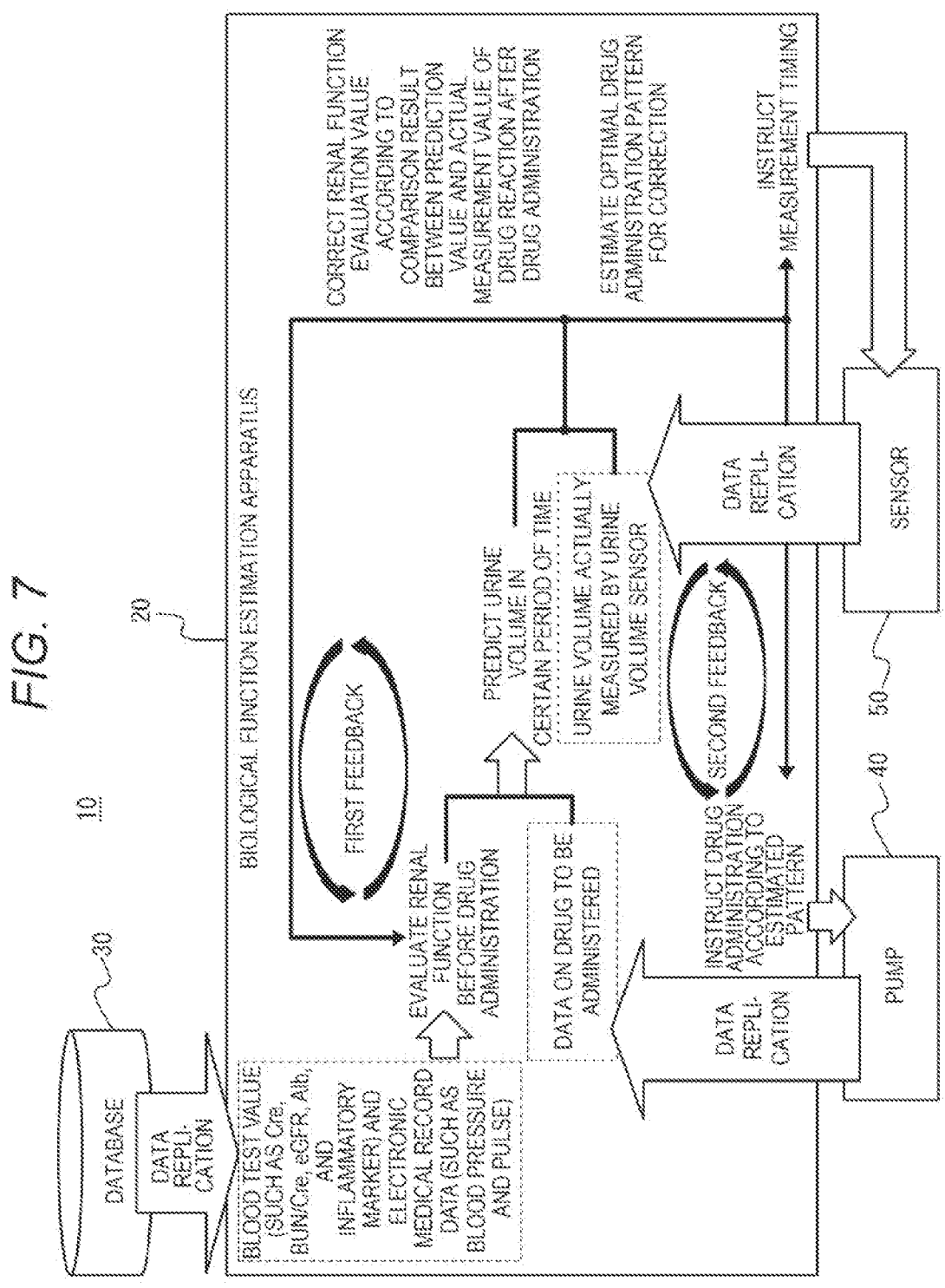
FIG. 7 is a diagram showing a configuration and functions of a system according to a third embodiment.

In the present embodiment, as shown in FIG. 7, in order to improve an evaluation accuracy on a renal function, an optimum drug administration pattern for correcting the evaluation value Ve is estimated, drug administration is instructed according to the estimated pattern, and a measurement timing of the urine volume is instructed. The drug administration pattern includes a procedure of bolus administration for rapidly administering a certain amount in addition to an increase or decrease in the administration amount within a predetermined prescription range or a procedure of stopping the administration, and a pattern in which a procedure of executing measurement by the sensor 50 according to a change in the drug administration pattern is repeated is selected.

Figure 8:
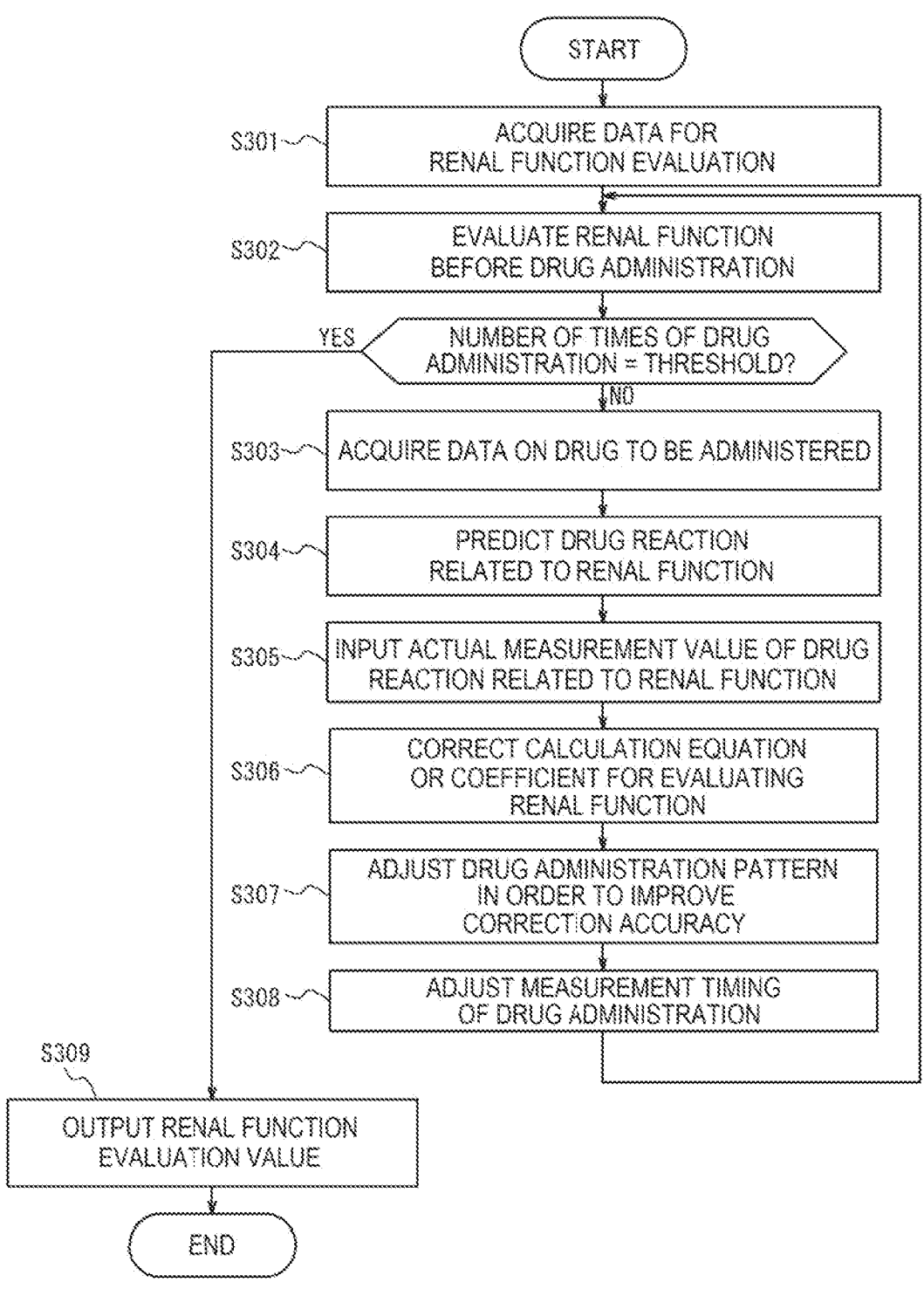
FIG. 8 is a flowchart showing an operation of a biological function estimation device according to the third embodiment.

An operation of the biological function estimation device 20 according to the present embodiment will be described with reference to FIG. 8.

In the present embodiment, a plurality of combinations of an estimation equation for calculating the evaluation value Ve from a comparison result between the prediction value Vp and the measurement value Vm in S302 and a drug administration pattern corresponding to the estimation equation are stored in the storage unit 22. Then, it is possible to obtain an evaluation value Ve with even higher accuracy by selecting an optimal drug administration pattern.

Since the processing of S301 to S306 is the same as the processing of S101 to S106 in the first embodiment, the description of S301 to S306 will be omitted.

In S307, the control unit 21 adjusts next and subsequent drug administration patterns according to a comparison result between the prediction value Vp obtained in S304 and the measurement value Vm obtained in S305. Specifically, the control unit 21 controls the pump 40 to set at least one of the number of times of administration of the drug and the administration amount per unit time of the drug, and sets a drug administration timing, thereby setting the drug administration pattern to the above pattern. Not only a drug administration time point, but also whether to stop the drug administration during continuous administration and whether to re-administer the drug when the drug administration is stopped may be set as the drug administration timing.

The urine volume per unit time is determined by a balance between the renal function and the drug administration amount. When the drug is a diuretic drug, the urine volume per unit time generally increases by increasing the administration amount, but an increasing tendency of the urine volume per unit can vary. The increasing tendency is represented by a slope or a plot shape, continuity in change, or presence or absence of a threshold when an administration amount of the diuretic agent is plotted on a horizontal axis and the urine volume is plotted on a vertical axis. The increasing tendency is closely related to the desired renal function. Therefore, within a predetermined prescription range, convergence patterns, which are different from one another, of a difference between the prediction value Vp and the measurement value Vm are obtained in a combination of the prediction value Vp and the measurement value Vm with respect to a urine volume responsiveness when the diuretic agent is bolus administered, a combination of the prediction value Vp and the measurement value Vm with respect to the urine volume responsiveness when the administration is stopped, and a combination of the prediction value Vp and the measurement value Vm with respect to fluctuation in the urine volume when the administration amount is intentionally increased or decreased. Then, three evaluation value Ve different from one another can be obtained. Since a degree of convergence in the difference between the prediction value Vp and the measurement value Vm differs depending on the difference in the drug administration pattern, the estimation accuracy as the renal function evaluation value differs among the three evaluation values Ve. Therefore, by preparing a plurality of combinations of the equation for calculating the evaluation value Ve from the prediction value Vp and the measurement value Vm and the drug administration pattern corresponding to the equation, the drug administration pattern in which the difference between the prediction value Vp and the measurement value Vm is sufficiently small when the processing of S302 to S308 is repeated can be selected as the optimal drug administration pattern for obtaining the evaluation value Ve with relatively high accuracy, and the target renal function evaluation value can be obtained.

In addition, by preparing the plurality of combinations of the equation for calculating the evaluation value Ve from the prediction value Vp and the measurement value Vm and a drug administration pattern corresponding to the equation, when the evaluation value Ve is calculated using a machine learning method, the plurality of combinations can be used as different explanatory variables. The explanatory variable is input information for estimating the evaluation value Ve. The plurality of combinations can be treated as individual regression trees in a random forest method, or can be used as a penalty term in machine learning. These methods are particularly effective in a case where, in each of the plurality of drug administration patterns, the difference between the prediction value Vp and the measurement value Vm converges sufficiently small and the evaluation value Ve is obtained, but the obtained evaluation values Ve are different from one another, and it is not possible to determine which evaluation value Ve is to be used.

When the processing of S302 to S308 are repeated, a combination of the prediction value Vp and the measurement value Vm are measured for each of various drug administration patterns. The obtained combination of the prediction value Vp, the measurement value Vm, and the evaluation value Ve is stored in the storage unit 22 in association with the drug administration pattern. In this case, the combination of the prediction value Vp, the measurement value Vm, and the evaluation value Ve may be stored, as time-series data, in the storage unit 22 in association with the drug administration pattern.

In S308, the control unit 21 adjusts a measurement timing of the urine volume as the drug reaction according to the drug administration pattern adjusted in S307. Specifically, the control unit 21 can control the sensor 50 to adjust the measurement timing of the urine volume so as to match the drug administration pattern adjusted in S307. In the present embodiment, when the drug administration pattern is changed, accurate measurement on the urine volume responsiveness corresponding to the drug administration pattern affects the estimation accuracy on the evaluation value Ve. Therefore, it is possible to obtain the evaluation value Ve with relatively high accuracy by executing the urine volume measurement so that the execution timings of the drug administration and the urine amount measurement coincide with each other.

Since the processing of S309 is the same as the processing of S107 in the first embodiment, the description of S309 will be omitted.

According to the present embodiment, since the renal function can be estimated using the urine volume responsiveness when the drug administration pattern is variously changed, the estimation accuracy on the renal function can be improved.

In the present embodiment, whether to execute the processing of S303 or the processing of S309 is selected depending on whether the number of times of administration of the drug reaches the threshold Vt. Alternatively, the difference between the prediction value Vp and the measurement value Vm may be used instead of the number of times of administration of the drug, as in the first embodiment. Alternatively, both the threshold Vt for the number of times of administration of the drug and the threshold for the difference between the prediction value Vp and the measurement value Vm may be used. In any case, the measurement may be executed by changing a plurality of types of drug administration patterns according to a predetermined pattern, or the drug administration pattern may be automatically selected from several candidates stored in advance in the storage unit 22 according to the value of the evaluation value Ve obtained after drug administration or variation in the evaluation value Ve obtained after the drug administration. In addition, by repeating the same drug administration pattern, the combination of the prediction value Vp and the measurement value Vm obtained for a specific drug administration pattern and the variation in the evaluation value Ve obtained thereafter may be reduced.

Further, as a result of executing the processing of S302 to S308 in some drug administration patterns, the prediction value Vp converges in any drug administration pattern, but when the difference between the prediction value Vp and the measurement value Vm does not become sufficiently small, the final evaluation value Ve may be obtained using a plurality of evaluation values Ve obtained for each drug administration pattern. In this case, any method can be selected as a method for obtaining the final evaluation value Ve. For example, an average value or a median value of the plurality of evaluation values Ve may be calculated as the final evaluation value Ve, or the final evaluation value Ve may be calculated by single regression analysis, multiple regression analysis, polynomial regression, or regularization.

In the storage unit 22, test results used at the time of renal function evaluation on different patients in the past, in-hospital data such as presence or absence of a basic disease, and a drug administration pattern effective for reducing the difference between the prediction value Vp and the measurement value Vm can be recorded in association with one another. When selecting an optimal drug administration pattern for a current target, similar patient information may be referred to from a test result used at the time of renal function evaluation on the current target and in-hospital data such as presence or absence of a basic disease, and a drug administration pattern effective for similar patients in the past may be preferentially selected. Further, the degree of convergence in the prediction value Vp or a decrease tendency itself of the difference between the prediction value Vp and the measurement value Vm for each drug administration pattern may be used as reference data, and the drug administration pattern effective in a similar case may be preferentially selected based on the past data stored in the storage unit 22.

Fourth Embodiment

Differences from the third embodiment will be mainly described.

Figure 9:
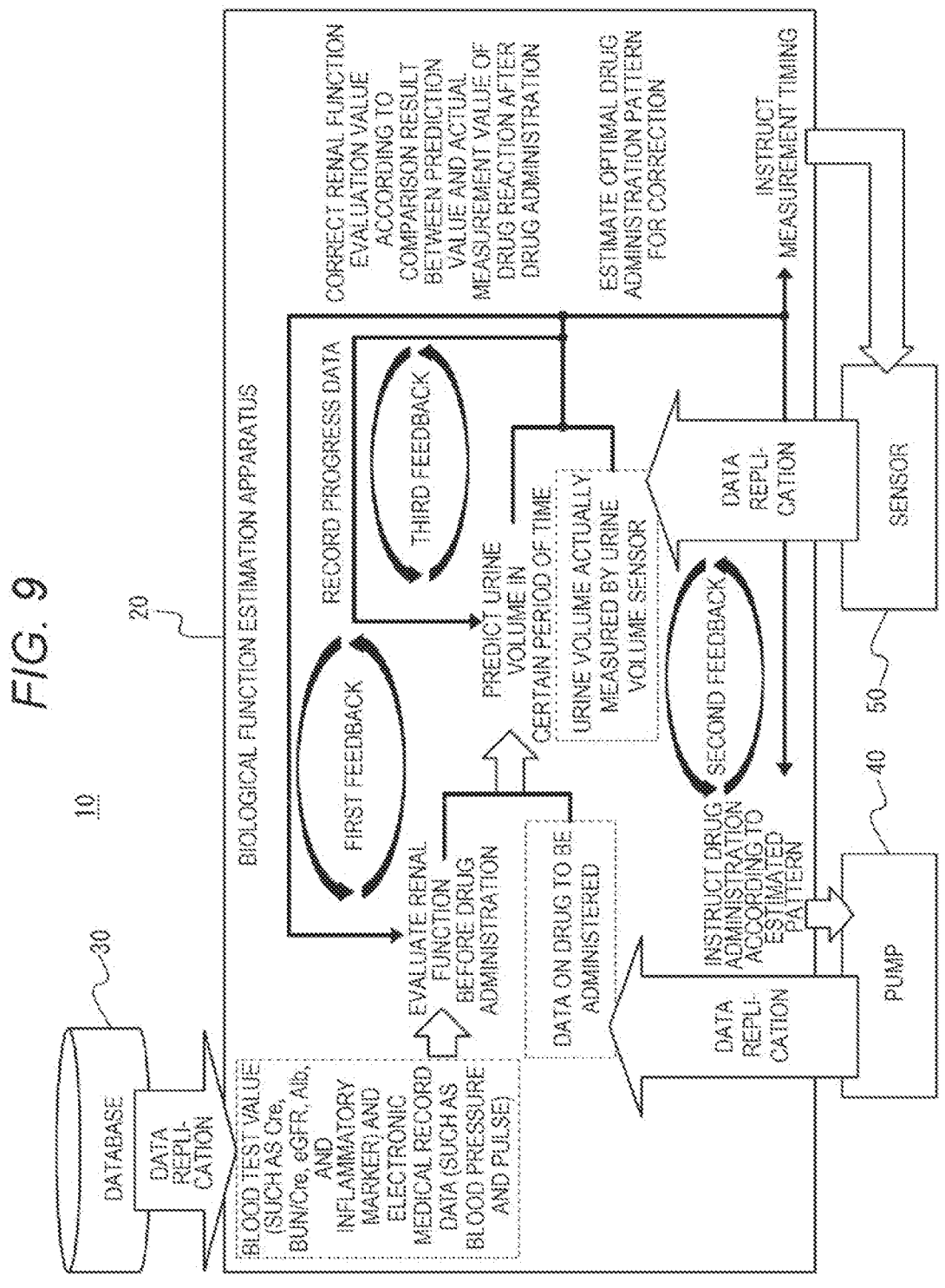
FIG. 9 is a diagram showing a configuration and functions of a system according to a fourth embodiment.

In the present embodiment, as shown in FIG. 9, progress data Dp on a drug reaction for specific drug administration is recorded. The progress data Dp can include data in which a change per day in a patient during hospitalization and a change at the time of rehospitalization from previous hospitalization are recorded. The progress data Dp is referred to at the time of predicting the drug reaction related to the renal function. The history indicated by the progress data Dp may include a history of another patient.

An operation of the biological function estimation device 20 according to the present embodiment will be described with reference to FIG. 10.

Since the processing of S401 to S403 are the same as the processing of S301 to S303 in the third embodiment, the description of S401 to S403 will be omitted.

In S404, when the control unit 21 predicts a urine volume as the drug reaction, the control unit 21 refers to the progress data Dp indicating the history of the past drug administration and drug reaction. Specifically, the control unit 21 analyzes the history indicated by the progress data Dp and extracts characteristics of the drug reaction unique to the patient. When the control unit 21 refers to a table stored in advance in the storage unit 22 and specifies the prediction value Vp, the control unit 21 corrects the specified prediction value Vp according to the characteristics of the drug reaction unique to the patient. Alternatively, when the control unit 21 applies a predefined equation and calculates the prediction value Vp, the control unit 21 corrects the calculated prediction value Vp according to the characteristics of the drug reaction unique to the patient.

Since the processing of S405 is the same as the processing of S305 in the third embodiment, the description of the S405 will be omitted.

In S406, the control unit 21 records, as a part of the progress data Dp, date and time of drug administration by the pump 40, a type and amount of the administered drug, and the measurement value Vm obtained in S405.

Since the processing of S407 to S410 are the same as the processing of S306 to S309 in the third embodiment, the description of S407 to S410 will be omitted.

According to the present embodiment, when the prediction value Vp is calculated, the progress data Dp can be referred to in addition to the data Dm on the drug and the various data for renal function evaluation including the measurement value Vm. Therefore, the prediction value Vp closer to a true value can be obtained. Therefore, the number of repetitions of the processing of S402 to S409 can be reduced, and a time required to output a renal function evaluation value in S410 can be shortened.

Reducing the number of repetitions of the processing of S402 to S409 and shortening the time required to output the renal function evaluation value in S410 is important in a situation such as ICU in which it is necessary to evaluate the renal function of the patient in real time.

That is, according to the present embodiment, since the prediction accuracy on the prediction value Vp based on the drug reaction is improved, the time required to output the renal function evaluation value can be shortened, and the estimation accuracy on the renal function can be maintained or improved even in a use method such as real-time monitoring.

As a modification of the present embodiment, the control unit 21 may update the progress data Dp each time the prediction value Vp and the measurement value Vm are obtained. Accordingly, the prediction value Vp closer to a true value can be obtained.

When combinations of the prediction value Vp and the measurement value Vm in various administration patterns applied in the past are stored as the progress data Dp indicating the history of past drug administration and drug reaction, the control unit 21 can obtain the prediction value Vp more individually optimized for a measurement target by executing machine learning using the combinations.

In the present embodiment, whether to execute the processing of S403 or the processing of S410 is selected depending on whether the number of times of administration of the drug reaches the threshold Vt. Alternatively, the difference between the prediction value Vp and the measurement value Vm may be used instead of the number of times of administration of the drug, as in the first embodiment. Alternatively, both the threshold Vt for the number of times of administration of the drug and the threshold for the difference between the prediction value Vp and the measurement value Vm may be used. In any case, when the processing of S402 to S409 is repeated, the progress data Dp is referred to for prediction of the drug reaction related to the renal function.

The present disclosure is not limited to the above embodiments. For example, a plurality of blocks described in the block diagram may be integrated, or one block may be divided. Instead of executing the plurality of steps described in the flowcharts in time series according to the description, the steps may be executed in parallel or in a different order as necessary or according to the processing capability of the device that executes the steps. In addition, modifications can be made without departing from the gist of the present disclosure.

The detailed description above describes embodiments of a biological function estimation device and a biological function estimation method. These disclosed embodiments represent examples of the biological function estimation device and the biological function estimation method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A biological function estimation system comprising:
   a biological function estimation device comprising a processor;
   a pump;
   the processor configured to:
   predict a drug reaction before a drug administration in a patient based on an evaluation value of a biological function obtained by evaluating the biological function of the patient from a test result before the drug administration and data on a drug to be administered to the patient, the drug reaction being urine volume per unit of time as measured by a urine volume sensor and the evaluation value is a value obtained by evaluating a renal function as the biological function; and correct the evaluation value according to a comparison result between an obtained prediction value, which is related to the drug reaction and different from the evaluation value, and a measurement value, which is related to the drug reaction and different from the evaluation value, obtained by measuring the drug reaction after the drug administration, wherein for drug administration at each of a plurality of time points, the processor is configured to:

set a drug administration pattern at each of the plurality of time points;

predict the drug reaction based on a corrected value of the evaluation value obtained for drug administration at any one of the plurality of time points and data on the drug to be administered to the patient at a next time point;

correct the corrected value of the evaluation value related to the drug reaction according to a comparison result between an obtained new prediction value and a new measurement value obtained by measuring the drug reaction after the drug administration at the next time point;

adjust, according to a comparison result between the new prediction value and the new measurement value obtained for drug administration, the drug administration pattern at a new next time point; and control the pump by setting at least one of the number of times of administration of the drug and an administration amount per unit time of the drug so as to administrate the drug according to an adjusted drug administration pattern at the new next time point; and wherein the pump administers the drug in accordance with the adjusted drug administration pattern.

2. The biological function estimation device according to claim 1, wherein the processor is configured to:

change at least one of an equation and a coefficient for calculating the evaluation value according to the comparison result.

3. The biological function estimation device according to claim 1, wherein the data includes at least one of a type of the drug, a total administration amount of the drug, and an administration amount per unit time of the drug.

4. The biological function estimation device according to claim 1, wherein the processor is configured to:

record, as temporary correction values, corrected values of the evaluation value obtained for drug administration at the plurality of time points; and correct the evaluation value using the recorded temporary correction values.

5. The biological function estimation device according to claim 1, wherein the processor is configured to:

select, as the pattern, a pattern candidate that is different for each time point from a predetermined pattern candidate group.

6. The biological function estimation device according to claim 1, wherein the processor is configured to:

set the pattern by setting at least one of the number of times of administration of the drug and an administration amount per unit time of the drug.

7. The biological function estimation device according to claim 1, wherein the processor is configured to:

set the pattern by setting a drug administration timing.

8. The biological function estimation device according to claim 1, wherein when setting the pattern, the processor is configured to:

refer to performance data indicating a history of past drug administration and at least one of a prediction value, a measurement value, and a corrected value of the evaluation value.

9. The biological function estimation device according to claim 8, wherein the history indicated by the performance data includes a history of another patient.

10. The biological function estimation device according to claim 1, wherein the processor is configured to:

adjust a measurement timing of the drug reaction according to the pattern.

11. The biological function estimation device according to claim 1, wherein when predicting the drug reaction, the processor is configured to:

refer to progress data indicating a history of past drug administration and drug reaction, and wherein the history indicated by the progress data includes a history of another patient.

12. The biological function estimation device according to claim 1, further comprising:

an output unit configured to output the corrected value of the evaluation value; and wherein the processor is configured to:

control the pump configured to administer the drug to the patient; and control the urine volume sensor configured to measure the urine volume per unit of time produced by the patient.

13. The biological function estimation device according to claim 1, wherein the processor is configured to:

acquire the test result; and calculate the evaluation value from the test result.

14. A biological function estimation method comprising:

predicting, by a processor, a drug reaction before drug administration in a patient based on an evaluation value of a biological function, which is obtained by evaluating a biological function of the patient from a test result before the drug administration and data on a drug to be administered to the patient to obtain a prediction value that is related to the drug reaction and different from the evaluation value, the drug reaction being urine volume per unit of time as measured by a urine volume sensor and the evaluation value is a value obtained by evaluating a renal function as the biological function;

administering the drug to the patient by a pump;

measuring, by the urine volume sensor, a urine volume per unit of time after the drug administration to obtain a measurement value that is related to the drug reaction and different from the evaluation value;

correcting, by the processor, the evaluation value according to a comparison result between an obtained prediction value and an obtained measurement value;

setting a drug administration pattern at each of the plurality of time points;

predicting the drug reaction based on a corrected value of the evaluation value obtained for drug administration at any one of the plurality of time points and data on the drug to be administered to the patient at a next time point;

correcting the corrected value of the evaluation value related to the drug reaction according to a comparison result between an obtained new prediction value and a new measurement value obtained by measuring the drug reaction after the drug administration at the next time point;

adjusting, according to a comparison result between the new prediction value and the new measurement value obtained for drug administration, the drug administration pattern at a new next time point;

controlling the pump by setting at least one of the number of times of administration of the drug and an administration amount per unit time of the drug so as to administrate the drug according to an adjusted drug administration pattern at the new next time point; and administering the drug to the patient in accordance with the adjusted drug administration pattern by the pump.

15. The biological function estimation device according to claim 1, wherein the processor is configured to:

set the drug administration pattern from a plurality of patterns, and wherein the plurality of patterns includes:

a pattern in which a dose of the drug is increased stepwise from a low dose within a predetermined prescription range; and a pattern in which the dose of the drug is decreased stepwise from a high dose within a predetermined prescription range.

16. The biological function estimation device according to claim 1, wherein the plurality of patterns further includes a pattern of bolus administration for rapidly administering a certain amount.

17. The biological function estimation device according to claim 1, wherein the processor is configured to:

set the drug administration pattern based on a drug administration pattern effective for similar patients by referring a similar patient information identified based on an evaluation test result of the biological function of the patient and in-hospital data indicating presence or absence of a basic disease of the patient.

18. The biological function estimation device according to claim 1, wherein the value obtained by evaluating the renal function as the biological function is solely based on the renal function of the patient before the drug administration.

19. The biological function estimation device according to claim 18, wherein the test result includes device measurement values and electronic medical record data of the patient before the drug administration.

* * * * *